United States Patent [19]

Ban et al.

[11] Patent Number: 4,956,347

[45] Date of Patent: Sep. 11, 1990

[54] USE OF SULFOMUCOPOLYSACCHARIDES IN THE TREATMENT OF ALZHEIMER-TYPE SENILE DEMENTIA

[75] Inventors: Thomas A. Ban, Nashville, Tenn.; Umberto Cornelli, Milan, Italy

[73] Assignee: Crinos Industria Farmacobiologica Spa, Como, Italy

[21] Appl. No.: 197,419

[22] Filed: May 23, 1988

[30] Foreign Application Priority Data

May 28, 1987 [IT] Italy .................................. 20698 A/87

[51] Int. Cl.$^5$ .................. A61K 31/715; A61K 31/725
[52] U.S. Cl. ...................................................... 514/54
[58] Field of Search .......................................... 514/54

[56] References Cited

U.S. PATENT DOCUMENTS 3,000,787  9/1961  Bianchini et al. .................... 424/104
3,007,787  12/1961  Campbell et al. ...................... 568/38

OTHER PUBLICATIONS

The Merck Manual, 14th Edition, 1982, pp. 1305–1309; "Dementia", Whole Article.

*Primary Examiner*—Ronald W. Griffin
*Assistant Examiner*—Pamela S. Webber
*Attorney, Agent, or Firm*—Armstrong, Nikaido, Marmelstein, Kubovcik & Murray

[57] ABSTRACT

The administration of ateroid alleviates the symptoms of Alzheimer-type senile dementia.

2 Claims, No Drawings

USE OF SULFOMUCOPOLYSACCHARIDES IN THE TREATMENT OF ALZHEIMER-TYPE SENILE DEMENTIA

The present invention relates to the therapeutical treatment of conditions of senile dementia of the Alzheimer type.

In the industrialized countries a progressive increase of the average age of the population is occurring with a more and more relevant presence of aged people older than 65 years. It is calculated that today in Europe 13% of the population is older than 65 years and that such a percentage shall increase by 20% by the year 2025.

It involves and shall involve in a greater measure in the future an increase of the incidence of the pathologies having as their base a reduced capacity of the cerebral function.

These pathologies, which cause a series of psychological and behaviour compromissions of more or less serious magnitude, shall by their nature become heavier and shall influence more and more the daily life of the affected individuals.

The problem, which starts from the single person, is rapidly extended to the family nucleus and then to the society as a whole.

The "cerebral pathology" which is manifested through a number of alterations of superior functions of the human being such as memory, alertness, social life, humour, has been given several more or less specific names.

Chronic Senile Cerebral Insufficiency (CSCI), Organic Brain Syndrome (OBS), Senile Dementia are representative of the most frequently recurring definitions given in the geriatric literature.

By using specific instruments such as the Hachinski scale and the DMS III (Diagnostic and Statistic Manual) and on the basis of the clinical anamensis, the cerebral pathologies defined as Senile Dementia of Alzheimer The (SDAT) and Multiinfarctual Dementia (MID) have acquired a more specific diagnostic meaning.

The accurate analysis of elderly patients showing the syndrome picture of the cerebral deficit, permit them to the classified, in most cases, as SDAT or MID patients and, within these two classes, the Alzheimer dementia represents the higher percentage of affected subjects.

Although the whole symptomatology, characterizing the patients affected by Alzheimer senile dementia and its evolution, is rather clear and defined, the etiology of the disease is not manifest as well. In this connection some assumptions have been made which refer to alterations of the immunological system, to the chronical toxicity as caused by polluting substances, e.g. aluminium, to the viral origin and more recently to the genetic origin, a relationship with problems of circulation and/or atherosclerosis, very frequent in the elderly person, being however always excluded.

The lacking of knowledge about the etiology of the Alzheimer disease has not defeated but on the contrary promoted a great number of attempts of therapeutical approach aiming to at least alleviate or slow down the course of the illness, even if no complete recovery is achieved, since this disease is often ravaging at the level of the individual and is a serious social problem.

The attempts of intervention on elderly patients are taking several forms.

In this context, there are considered as valid approaches not only those of psychological and emotional nature, which are to be always present, but also those carried out by pharmacological therapies.

A first therapeutical approach has been that of the so-called "cerebral vasodilators".

For this class of drugs several mechanisms have been suggested going from the direct action on the vasal smooth muscles (nicotinic acid and derivatives thereof, papaverine, calcium antagonists) to the alfa-blocking action (ergot alkaloids).

These drugs have little by little lost importance both because in the meanwhile the mechanisms of self-adjustment of the cerebral vascularization, differing from those present at the level of circulation generically meant, were meanwhile clarified and because, for some of them, the vasodilating action, being not specific for the brain, might even cause the conditions of cerebral perfusion to worsen owing to the occurrence of the hematic "theft". Recently the remarkable limits of use of the flunarizine have been detected, which, for treatments even not extended, leads to side effects at the level of the cerebral nervous system (SNC), such as the sedation and the parkinsonism which tend to worsen the symptomatology in the elderly patient.

As the experimental research work has progressed, other relevant features have been detected relating to the cerebral aging.

From the evaluation and the intervention on the circulation, the attention has been moved to the metabolism of the nervous tissues and to the neurochemistry of the synaptic receptors.

In this context attempts have been made, looking for an enhancement of the cholinergic transmission, which is seemingly one of the most compromised functions in the Alzheimer disease.

The use of precursors of acetylcholine, however, has given not satisfactory results, since the cholinergic deficit is not so much connected to the lacking of substrate (choline) but to the lacking of cholinacetyl transferase enzyme, which is the limiting factor in the acetylcholine synthesis.

These drugs, moreover, being to date available only for parenteral treatments, find an objective limitation in the impossibility of being used for long treatment periods. It is instead known that for the cerebral pathology, by its nature, no recovery is possible, but it requires a constant and ad vitam treatment. In the process of cerebral aging the catecholaminergic transmission undergoes a slowing down, as caused by the progressive decrease of the neuromediators.

Starting from the experimental evidences drugs have been employed capable of directly or indirectly stimulating the dopaminergic and serotoninergic receptors.

The uncertainties in the knowledge about the etiopathogenesis of the cerebral pathology, in general, and of the Alzheimer type dementia, in particular, lead to the wide spectrum of pharmacological interventions, such as opium agonists and antagonists, polypeptides, iron and aluminium chelating ligands, serotoninomimetics, phospholipids, etc.

Notwithstanding that the studies on the above mentioned drugs are large and well documented, it is however believed that for none of them the clinical efficay is enough proved, taking also it into account that an extended therapy, as usually requried for such a pathology, in many cases does limit the use of these substances owing to the occurrence of side effects, which by the way have been already mentioned.

The mixtures of sulfomucopolysaccharides obtained by extraction from animal organs are known.

One of them, the preparation of which in detailedly described in the U.S. Pat. No. 3,000,787 (which is herein enclosed by reference) is the active ingredient of a drug which since a number of a years is therapeutically used and sold in Italy under the name Ateroid; it is used in the treatment of atherosclerosis, lipidic metabolism and peripheral arteriopaties.

This drug, both in the clinical practice and through proper research work, has proven to be particularly useful since a confirmed efficacy in the above mentioned pathologies is combined with a very low toxicity permitting the extended use of the active principle at high dosages. As an example in the following table I the results of the experiments for the assessment of acute, subacute and chronic toxicity are reported.

TABLE I

Toxicity of Ateroid according to experimental models in the animal

| Type of toxicity | animal | administration route | found values and/or doses* | remarks |
|---|---|---|---|---|
| $LD_{50}$ | mouse | per os | 5,000 | — |
|  |  | i.p. | 3,000 | — |
|  | rat | per os | 5,000 | — |
|  |  | i.p. | 3,000 | — |
|  | dog | per os | 5,000 | — |
|  |  | i.p. | 1,000 | — |
| Subacute toxicity (4 weeks) | rat | per os | min. 250 max. 1000 | all the animals survived, the bioumoral parameters remain in the standard ranges |
|  | dog | s.c. | min. 100 max. 200 | all the animals survived, the bioumoral parameters remain in the standard ranges |
| Chronic toxicity | rat | per os | min. 100 max. 200 | all the animals survived, the bioumoral parameters remain in the standard ranges |
| (9 months) | dog | i.m. | min. 25 max. 100 | all the animals survived, the bioumoral parameters remain in the standard ranges |
| (5 months) | dog | per os | min. 50 max. 200 | all the animals survived, the bioumoral parameters remain in the standard ranges |

*in LPL-RU/kg

As it can be noticed, the results are indicated as LPU-RU/kg, wherein the abbreviation LPU-RU indicates LipoProteinLipase Releasing Unit and relates to the quantitative method of biological dosing of this active principle, which is based on an effect provoked by the drug in the circulatory system, namely the liberation in the blood stream of the lipoproteinlipase enzyme which is active on the ester bonds of the triglycerides. Then, through the action of the enzyme on a suitable substrate the biological actitivity LPU-RU of the sulfomucopolysaccharides can be measured by indirect way. As a matter of practive such a measurement is carried out by incubating with a suitable lipidic substrate the plasma of rats treated with the drug and evaluating the absorbance fall of the plasma substrate system.

The conventional unit LPU-RU is thus defined as that amount of substance which upon being injected by intravenous route liberates in circulation an amount of enzyme capable of inducing a 50% fall of the absorbance of the plasma-substrate system after 15 minutes of incubation at 25° C.

Said mixture of sulfomucopolysaccharides is also standardized through the routine evalutaion of several chemical parameters. The analytical profile is reported in table II.

TABLE II

Main analytical parameters of the mixture of sulfomucopolysaccharides

| Biological activity (LPL-RU) | 8–15 LPL-RU |
|---|---|
| Hexuronic acids | 28–35% |
| hexosamines | 23–30% |
| organic sulfur | 7–9% |
| proteins | absent |
| proteic derivatives | less than 3% |
| other impurities | within the limits. |

Analytical investigations have shown that the sulfomucopolysaccharides present in the mixture are the following: heparin, heparan sulfate like substance, dermatan sulfate and chondroitin sulfate A and C. It has been now suprisingly found and it is subject of the present invention that the administration of the sulfomucopolysaccharide mixture as above defined to patients suffering from Alzheimer type senile dementia permits remarkable improvements of the clinical symptomatology of the disease to be achieved.

Otherwise stated, nothing of what was known might induce the supposition that a drug, indicated in the treatment of diseases like the arteriosclerosis, exclusively related to phenomena of throttling up to occlusion of the blood vessels, might be efficacious in this pathology, as confirmed by the experiments, as hereinafter reported, carried out on human volunteers.

For the treatment of the Alzheimer disease according to the present invention the administration is foreseen of the mixture of sulfomucopolysaccharides as above defined by oral route (tablets, capsels, etc.) or by injection (vials for intramuscolar and/or intravenous use) with daily dosage corresponding to 250–500 LPU-RU and with chronical administration. The experimental study has been carried out on 26 patients, with diagnosis of Alzheimer-type senile dementia, on the average being 69.5 years old.

The admission criteria were the following:
age of 60 years or more;
SDAT diagnosis according to the criteria of DMS III (Americal Psychiatric Association; Diagnostic and Statistical Manual of Mental Disorders, 3rd Edition, Washington D.C., Author. 1980).

A score less than 4 of the "Ischemic Score of Hachinski" (Hachinski V.C. et Alii "Cerebral Blood flow in dementia", Arch. Neurol. 32, 632–637 1975).

A score of between 3 and 7 in the Pfeiffer scale (Pfeiffer E. "A short portable mental status questionnaire for the assessment of organic brain deficiency in elderly patients" J. Am. Geratric Soc. 23 433–441, 441, 1975).

A score of between 3 and 5 in at least six SCAG Parameters (Shader R. I. et al. "A new scale for clinical assessment in geriatric populations" Sandoz Clinical Assessment Geriatric—SCAG-J.Am. Geriatric Soc. 22 107–113 1974).

The patients could not be admitted if, on the basis of the clinical anamnesis, were affected by serious diseases, such as tumors, metabolic disorders, diabetics, cardiac insufficiency, hyper or hypotension, arteriosclerosis, renal insufficiency, hepatic insufficiency, dependency an alcohol or opium substances, endocrinous disorders, epilepsy, peptic ulcer, neurological or psychiatric disorders besides the foreseen diagnosis (SDAT).

The experiments have been planned in two phases. A first phase was that of the so-called washing during which any treatment which weight have an action at the level of the central nervous system was suspended and a placebo was administered in form of a solution in vials for intramuscular use, which were fully undistinguishable as regards the physical aspect from the drug.

In the second phase, in which the treatment with the drug occurred the patients were administered with a dose corresponding to 250 or 500 LPL-RU/day for a period of 12 weeks.

All the patients have been evaluated according to the CGC scale or Global Clinical Judgement (Guy W. et Alii. "Assessment Manual Of Psychopharmacology". Revised 1976 DHEW publication n. (ADM) 76-338 Rockwille, MD, 1976).

Such judgement has been given five times during the experimental work, i.e. at the end of the washing treatment and respectively after 4,8 and 12 weeks of treatment with Ateroid. This GCG evaluation involves a threefold evaluation: seriousness of the symptomatology, degree of global improvement consequent to the treatment, index of efficaciousness/tolerability of the treatment.

The parameter "seriousness of the symptomatology" indicates the global seriousness of the patient and is defined by a score of 1 to 7 (1=normal conditions; 7=extremely serious situation). This parameter is evaluated throughout the treatment.

The parameter "global improvement" indicates the global change of the patient conditions and is evaluated by a score from 1 (highly improved) to 7 (highly worsened), the score 4 indicating no changes with respect to the evaluation before the treatment is started.

This parameter is taken into consideration in the times subsequent to the starting of the therapy (4,8 and 12 weeks of treatment).

The patients have been also evaluated according to other investigating methods such as the Plutchick scale and the Hamilton scale relating to the depression, in order to point out possible activities of the drug at the psychological and behavioural level.

The results have shown significant improvements of the patient status. The clinical evaluation on the seriousness of the symptomatology, expressed as above indicated, has shown a reduction of 13%, passing from the initial score (before the treatment) of 4.5 to a final value (after three months treatment) of 3.9. The difference is statistically significant.

Though the global clinical judgement on the clinical improvement it has been assessed that an improvement occurred in 65% of the patients, whereas for the remaining 34% the treatmet was not beneficial. The evaluation of the results obtained by considering the efficaciouness/tolerability ratio confirmed these conclusions.

The results obtained according to the geriatric scales of Plutchick and of Hamilton did show an improvement of some aspects of the behaviour of the patients, such as the alertness status, the ease, the sleep disorders, the sensorial disorders, the depression of the tone and the humour.

We claim:

1. A method for the treatment of a patient suffering from Alzheimer-type senile dementia which comprises administering to the pateint 250-500 LPU-RU of ateroid per day to reduce the symptoms of said senile dementia.

2. A method according to claim 1, wherein the ateroid is administered orally.